United States Patent
Yajima

(10) Patent No.: US 8,941,086 B2
(45) Date of Patent: Jan. 27, 2015

(54) CHARGED PARTICLE BEAM IRRADIATION APPARATUS

(71) Applicant: Sumitomo Heavy Industries, Ltd., Tokyo (JP)

(72) Inventor: Satoru Yajima, Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 14/272,596

(22) Filed: May 8, 2014

(65) Prior Publication Data

US 2014/0246606 A1    Sep. 4, 2014

Related U.S. Application Data

(63) Continuation of application No. PCT/JP2012/080738, filed on Nov. 28, 2012.

(30) Foreign Application Priority Data

Dec. 28, 2011    (JP) .................. 2011-287810

(51) Int. Cl.
| | |
|---|---|
| A61N 5/00 | (2006.01) |
| G21G 5/00 | (2006.01) |
| G21K 5/04 | (2006.01) |
| G21K 5/10 | (2006.01) |
| A61N 5/10 | (2006.01) |

(52) U.S. Cl.
CPC .. *G21K 5/04* (2013.01); *G21K 5/10* (2013.01); *A61N 5/1081* (2013.01); *A61N 2005/1087* (2013.01)
USPC .................. 250/492.3; 250/492.1; 250/493.1; 250/396 R; 250/398

(58) Field of Classification Search
USPC ............ 250/492.1, 492.3, 493.1, 396 R, 398
See application file for complete search history.

(56) References Cited

U.S. PATENT DOCUMENTS

| | | | | |
|---|---|---|---|---|
| 4,885,998 | A | * | 12/1989 | Span et al. ..................... 108/139 |
| 2005/0161618 | A1 | * | 7/2005 | Pedroni ...................... 250/492.3 |
| 2011/0101246 | A1 | * | 5/2011 | Yajima et al. .............. 250/492.3 |

FOREIGN PATENT DOCUMENTS

| | | |
|---|---|---|
| JP | 2005-538785 A | 12/2005 |
| JP | 2011-092424 A | 5/2011 |

OTHER PUBLICATIONS

Eros Pedroni, "Improving Gantry-Based Proton Scanning Beyond the Current State of the Art," Center for Proton Therapy, Paul Scherrer Institute, Switzerland, 29ESTRO Sep. 12-16, 2010, Barcelona, Spain.
International Search Report dated Jan. 15, 2013 corresponding to International Patent Application No. PCT/JP2012/080738.
International Preliminary Report dated Jul. 10, 2014, for corresponding International Application No. PCT/JP2012/080738.

* cited by examiner

*Primary Examiner* — David Porta
*Assistant Examiner* — Meenakshi Sahu
(74) *Attorney, Agent, or Firm* — Squire Patton Boggs (US) LLP

(57) ABSTRACT

A charged particle beam irradiation apparatus includes: an irradiation section configured to irradiate an irradiated body with a charged particle beam; a gantry in which an irradiation section is disposed and which can rotate or oscillate around a central axis line; an enclosure in which the irradiated body is disposed; and a gantry-side transport line that has an inlet section on which a charged particle beam emitted from an accelerator is incident and that is supported on the gantry and configured to transport an incident charged particle beam to the irradiation section, in which the gantry has a first bearing section provided between the inlet section of the gantry-side transport line and the enclosure, and a second bearing section provided on a side opposite to the first bearing section with respect to the enclosure.

3 Claims, 3 Drawing Sheets

CHARGED PARTICLE BEAM IRRADIATION APPARATUS

INCORPORATION BY REFERENCE

Priority is claimed to Japanese Patent Application No. 2011-287810, filed Dec. 28, 2011, and International Patent Application No. PCT/JP2012/080738, the entire content of each of which is incorporated herein by reference.

BACKGROUND

1. Technical Field

The present invention relates to a charged particle beam irradiation apparatus for irradiating an irradiated body with a charged particle beam.

2. Description of the Related Art

As a charged particle beam irradiation apparatus which performs radiation therapy for cancer or the like, a charged particle beam irradiation apparatus which is provided with an irradiation section which irradiates cancer or the like with a charged particle beam and a gantry in which the irradiation section is disposed and which can oscillate around a central axis line within a predetermined angle is known in the related art. In such a charged particle beam irradiation apparatus, since it is possible to change an irradiation angle of the irradiation section by a change in the angle of the gantry, it is possible to irradiate the charged particle beam at an appropriate angle corresponding to the position of cancer or the like.

SUMMARY

According to an embodiment of the present invention, there is provided a charged particle beam irradiation apparatus including: an irradiation section configured to irradiate an irradiated body with a charged particle beam; a gantry in which the irradiation section is disposed and which can rotate or oscillate around a central axis line; an enclosure which has a tubular side wall extending along the central axis line, vertical walls provided at both ends in a direction along the central axis line of the side wall, and an opening portion provided at a portion of the side wall and in which the irradiated body is disposed inside thereof and a gantry-side transport line that has an inlet section on which the charged particle beam emitted from an accelerator is incident and that is supported by the gantry and configured to transport the charged particle beam incident from the inlet section, to the irradiation section, wherein the gantry has a first bearing section which is provided between the inlet section of the gantry-side transport line and the enclosure and supports the gantry so as to be able to rotate or oscillate, and a second bearing section which is provided on a side opposite to the first bearing section with respect to the enclosure and supports the gantry so as to be able to rotate or oscillate.

DETAILED DESCRIPTION

Figure 1:
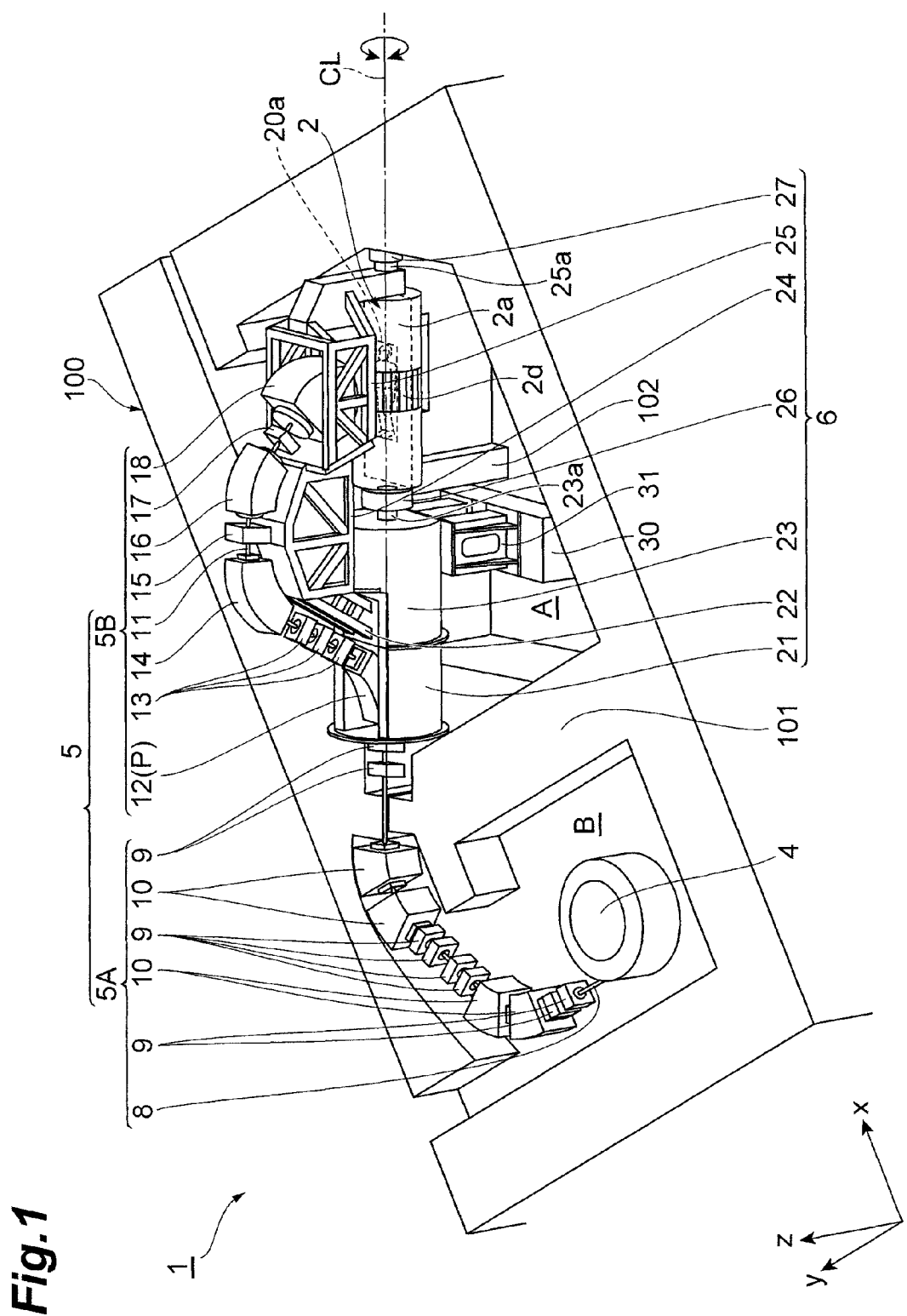
FIG. 1 is a perspective view showing a charged particle beam irradiation apparatus according to an embodiment of the present invention.

In the charged particle beam irradiation apparatus of the related art described above, because of the influence of mechanical backlash or the weight of the irradiation section or the gantry itself, there is a problem in that the isocenter accuracy of the charged particle beam irradiation apparatus is reduced according to a change in the angle of the gantry.

It is desirable to provide a charged particle beam irradiation apparatus in which it is possible to improve isocenter accuracy.

According to the charged particle beam irradiation apparatus related to the embodiment of the present invention, since the first and second bearing sections supporting the gantry are provided at positions to sandwich the enclosure therebetween, compared to the apparatus of the related art in which a bearing section is provided on only one side of the enclosure, it is possible to accurately retain the gantry and the irradiation section in the vicinity of the enclosure. As a result, since it is possible to suppress a deviation of the isocenter position of the irradiation section due to a change in the angle of the gantry, it is possible to improve the isocenter accuracy of the apparatus. Further, since the enclosure has the tubular side wall extending along the central axis line and the opening portion provided at a portion of the side wall, a patient can enter the enclosure from the side of the enclosure rather than from a direction along the central axis line. That is, it is not necessary to provide a space for a patient entering the enclosure on the end portion side in the direction along the central axis line of the charged particle beam irradiation apparatus in the irradiation chamber. By installing the second bearing section in the space which becomes omissible, it is possible to suppress an increase in the size of the irradiation chamber in the direction along the central axis line and improve the isocenter accuracy of the apparatus.

In the charged particle beam irradiation apparatus according to the embodiment of the present invention, the gantry may be disposed in a rectangular irradiation chamber such that the central axis line follows one diagonal line of the irradiation chamber.

According to the charged particle beam irradiation apparatus described above, in a case where the irradiation chamber has a rectangular shape, if the gantry is disposed in the irradiation chamber such that the central axis line follows one diagonal line of the irradiation chamber, since a patient can enter the enclosure by using a space in a direction along the other diagonal line, an increase in the size of the irradiation chamber can be further suppressed.

In the charged particle beam irradiation apparatus according to the embodiment of the present invention, the charged particle beam irradiation apparatus may further include a counterweight configured to balance rotation or oscillation of the gantry, and a counterweight connection section which is disposed between the inlet section of the gantry-side transport line and the enclosure and connects the gantry and the counterweight.

According to the charged particle beam irradiation apparatus described above, the charged particle beam irradiation apparatus is provided with the counterweight, whereby it is possible to stabilize the rotation or the oscillation of the gantry. In addition, according to the charged particle beam irradiation apparatus described above, since the counterweight connection section is disposed at an area between the inlet section of the gantry-side transport line and the enclosure, where it is easy to secure a space in a design, it is advantageous for a reduction in the size of the entire apparatus.

Hereinafter, a preferred embodiment of a charged particle beam irradiation apparatus according to the present invention will be described in detail with reference to the drawings.

Figure 2:
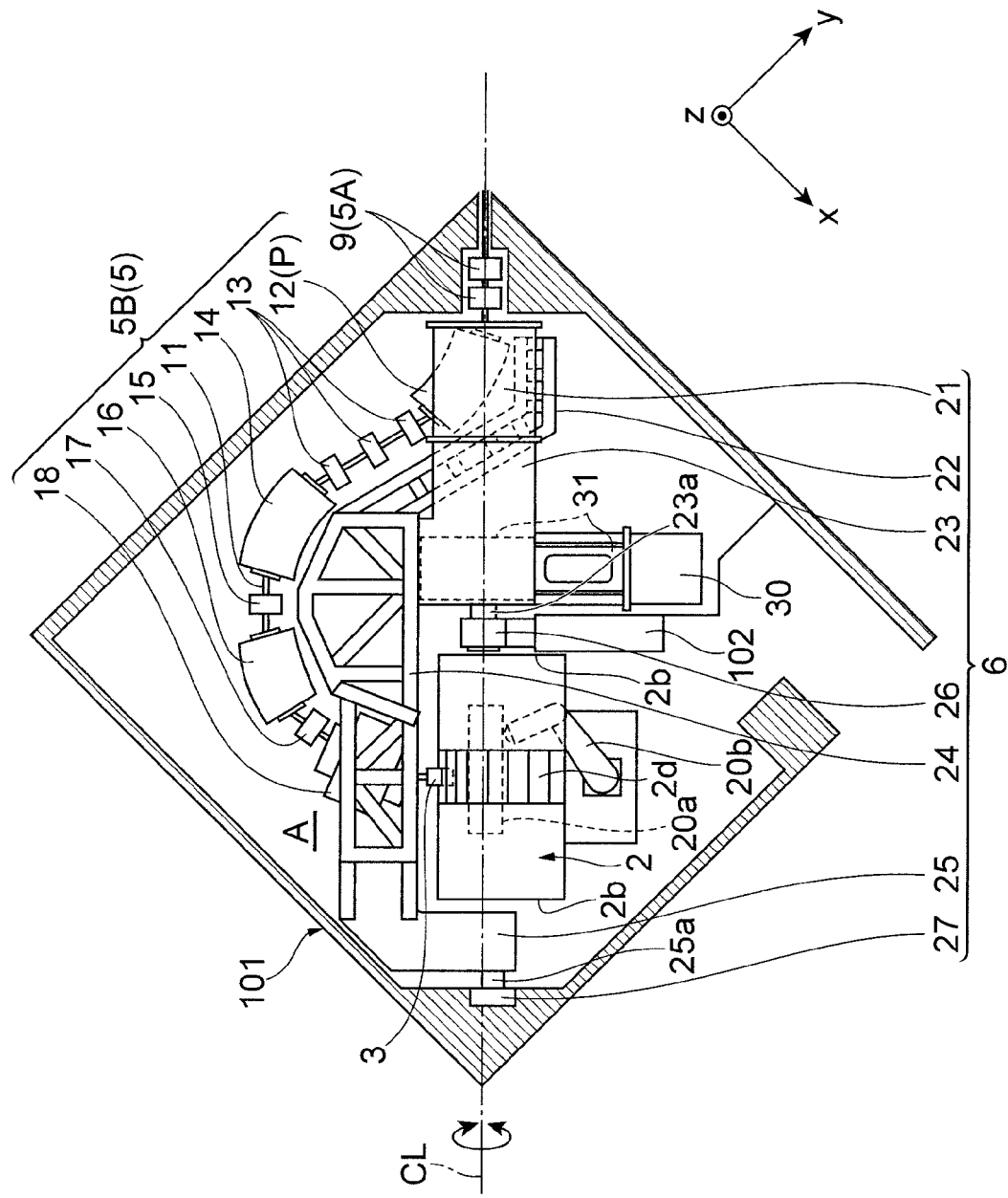
FIG. 2 is a plan view showing a state where a gantry in FIG. 1 is rotated by 90° and located in a horizontal plane.

As shown in FIGS. 1 and 2, a charged particle beam irradiation apparatus 1 according to this embodiment is an apparatus for performing radiation therapy by irradiating a charged particle beam from an irradiation section 3 with respect to a tumor or the like (an irradiated body) of a patient in an enclosure 2.

The charged particle beam irradiation apparatus 1 has, in a building 100, an accelerator 4 which accelerates charged particles and emits a charged particle beam, a transport line 5 which transports the charged particle beam emitted from the accelerator 4 to the irradiation section 3, and a gantry 6 which can oscillate around a central axis line CL.

The building 100 is separated into an irradiation chamber A and an accelerator chamber B by a partition wall 101. The gantry 6 and the enclosure 2 are disposed in the irradiation chamber A, and the accelerator 4 is disposed in the accelerator chamber B. The transport line 5 is provided to extend over both the irradiation chamber A and the accelerator chamber B.

The accelerator 4 is a device for emitting, for example, a proton beam, a heavy particle (heavy ion) beam, or the like as the charged particle beam. As the accelerator 4, for example, a cyclotron, a synchrotron, a synchrocyclotron, or a linear accelerator can be used. In terms of reduction in size, it is particularly preferable to adopt a superconducting cyclotron.

The transport line 5 transports the charged particle beam emitted from the accelerator 4 to the irradiation section 3. The transport line 5 is configured to include an accelerator-side transport line 5A and a gantry-side transport line 5B. Hereinafter, description will be made with the accelerator 4 side of the transport line 5 as an upstream side and the irradiation section 3 side as a downstream side.

The accelerator-side transport line 5A is a transport line which is connected to the accelerator 4 of the accelerator chamber B and fixed to the building 100. The accelerator-side transport line 5A is provided with an accelerator-side vacuum duct 8, an accelerator-side converging electromagnet 9, and an accelerator-side deflection electromagnet 10.

The accelerator-side vacuum duct 8 connects the accelerator 4 and the gantry-side transport line 5B. The charged particle beam emitted from the accelerator 4 is transported to the gantry-side transport line 5B through the accelerator-side vacuum duct 8.

The accelerator-side converging electromagnet 9 is disposed along the accelerator-side vacuum duct 8 and suppresses diffusion of the charged particle beam during transport. As for the accelerator-side converging electromagnet 9, a total of eight accelerator-side converging electromagnets 9 are provided. Four accelerator-side converging electromagnets among the accelerator-side converging electromagnets 9 are disposed so as to be sandwiched between two sets of accelerator-side deflection electromagnets 10. The remaining four accelerator-side converging electromagnets 9 are disposed by two on each of the upstream side and the downstream side of the two sets of accelerator-side deflection electromagnets 10.

The accelerator-side deflection electromagnet 10 performs the deflection of a traveling direction of the charged particle beam. The accelerator-side deflection electromagnets 10 are disposed two by two so as to sandwich the four accelerator-side converging electromagnets 9 therebetween on the accelerator-side vacuum duct 8. The accelerator-side deflection electromagnets 10 deflect the traveling direction of the charged particle beam along the accelerator-side vacuum duct 8.

The gantry-side transport line 5B is a transport line which is connected to the irradiation section 3 and fixed to the gantry 6. The gantry-side transport line 5B moves around the central axis line CL, being combined together with the gantry 6.

The gantry-side transport line 5B is provided with a gantry-side vacuum duct 11, a first gantry-side deflection electromagnet 12, a gantry-side converging electromagnet 13, a second gantry-side deflection electromagnet 14, a first scanning electromagnet 15, a third gantry-side deflection electromagnet 16, a second scanning electromagnet 17, and a fourth gantry-side deflection electromagnet 18.

The gantry-side vacuum duct 11 connects the accelerator-side vacuum duct 8 of the accelerator-side transport line 5A and the irradiation section 3 and configures a passage for the charged particle beam. The first gantry-side deflection electromagnet 12 is an electromagnet which deflects the traveling direction of the charged particle beam incident from the accelerator-side vacuum duct 8 along the central axis line CL, in a direction away from the central axis line CL. The first gantry-side deflection electromagnet 12 deflects the traveling direction of the charged particle beam in a direction inclined by 60° from the central axis line CL.

The first gantry-side deflection electromagnet 12 and the gantry-side vacuum duct 11 in the first gantry-side deflection electromagnet 12 configure an inlet section P connected to the accelerator-side transport line 5A.

The gantry-side converging electromagnet 13 includes three electromagnets which converge the beam diameter of the charged particle beam deflected by the first gantry-side deflection electromagnet 12. The charged particle beam converged by the gantry-side converging electromagnets 13 advances to the second gantry-side deflection electromagnet 14.

The second gantry-side deflection electromagnet 14 deflects the traveling direction of the charged particle beam by 60° in a direction along the central axis line CL. The charged particle beam deflected by the second gantry-side deflection electromagnet 14 advances to the first scanning electromagnet 15. The first scanning electromagnet 15 performs the scanning of the charged particle beam in a direction directed to the traveling direction of the charged particle beam passing through the inside thereof.

The third gantry-side deflection electromagnet 16 deflects the traveling direction of the charged particle beam scanned by the first scanning electromagnet 15 by 45° in a direction approaching the central axis line CL. The charged particle beam deflected by the third gantry-side deflection electromagnet 16 advances to the second scanning electromagnet 17. The second scanning electromagnet 17 performs the scanning of the charged particle beam in a direction orthogonal to the traveling direction of the charged particle beam passing through the inside thereof and also orthogonal to a scanning direction in the first scanning electromagnet 15.

The fourth gantry-side deflection electromagnet 18 deflects the traveling direction of the charged particle beam scanned by the second scanning electromagnet 17 by 45° in a direction orthogonal to the central axis line CL. The fourth gantry-side deflection electromagnet 18 is the final deflection electromagnet configuring the gantry-side transport line 5B. The charged particle beam deflected by the fourth gantry-side deflection electromagnet 18 is supplied to the irradiation section 3.

Figure 3:
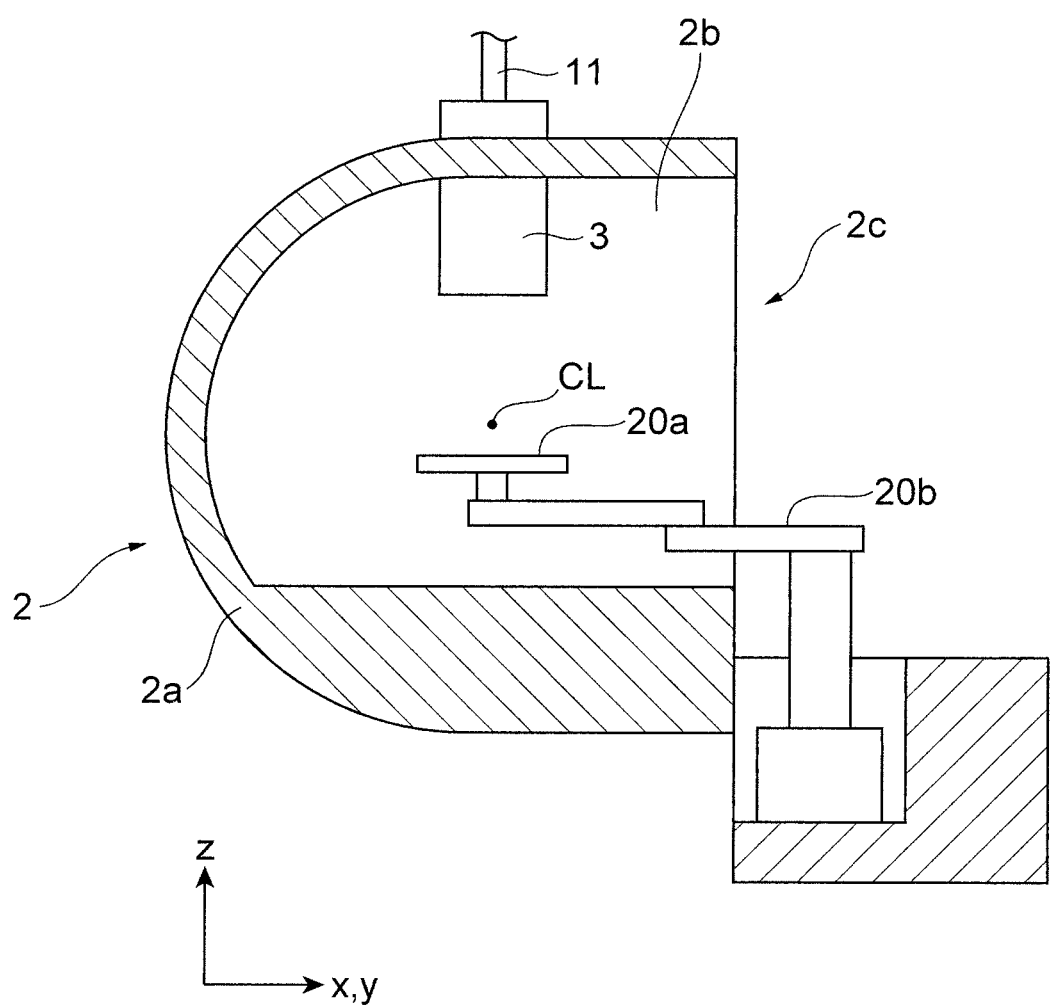
FIG. 3 is a cross-sectional view showing an enclosure in FIG. 1.

The irradiation section 3 performs the irradiation of the charged particle beam with respect to a tumor of a patient disposed on a treatment table 20a in the enclosure 2. The enclosure 2 has a tubular side wall 2a extending along the central axis line CL and is formed so as to surround the central axis line CL (refer to FIG. 3). Both ends in a direction along the central axis line CL of the side wall 2a are closed by vertical walls 2b perpendicular to the central axis line CL. An opening portion 2c is provided at a portion of the side wall 2a, and when viewed from the direction along the central axis line CL, the side wall 2a has a U-shape opened toward the side. A patient or a doctor can come and go between the irradiation chamber A and the inside of the enclosure 2 through the opening portion 2c. A portion of the side wall 2a is made as a moving wall 2d and the irradiation section 3 passes through the moving wall 2d. The side wall 2a is fixed to the building 100. However, the moving wall 2d is made so as to be movable along with the irradiation section 3 rotating around the central axis line CL according to the rotation of the gantry 6. The enclosure 2 has a sufficient length in an extending direction of the central axis line CL and has an open configuration such that a patient disposed on the treatment table 20a does not feel cooped-up.

The treatment table 20a in the enclosure 2 is movably supported by a six-axis articulated robot arm 20b. The six-axis articulated robot arm 20b accurately controls the position or the posture of the treatment table 20a according to a treatment plan.

The gantry 6 is configured so as to be able to oscillate around the central axis line CL. FIG. 1 shows the gantry 6 in a posture in which the gantry 6 stands in the vertical direction. FIG. 2 shows the gantry 6 in a posture in which the gantry 6 is rotated by 90° from the state of FIG. 1, and thus the gantry-side transport line 5B is located in a horizontal plane. The gantry 6 is configured so as to be able to oscillate in a range of 90° downward (in a direction in which the gantry-side transport line 5B is directed further downward than the horizontal plane) and 110° upward (in a direction in which the gantry-side transport line 5B is directed further upward than the horizontal plane) on the basis of the angle of the posture shown in FIG. 2. In the gantry 6 according to this embodiment, an upper angular range is set to be 110° rather than 90°, whereby the need for the posture of a patient to be changed for oblique irradiation at a slight angle is avoided, and thus the convenience of the apparatus is enhanced.

The gantry 6 is provided with an inlet-side support section 21, a ladder section 22, a shaft holding section 23, a central casing section 24, a leading end casing section 25, a first bearing section 26, and a second bearing section 27. Hereinafter, description will be made with the accelerator-side transport line 5A side in the extending direction of the central axis line CL as a rear side and the opposite side as a front side.

The inlet-side support section 21 is a site which supports the inlet section P of the gantry-side transport line 5B. The inlet-side support section 21 is fixed to the ladder section 22 provided along the gantry-side transport line 5B. The inlet-side support section 21 supports the inlet section P of the gantry-side transport line 5B, being combined together with the ladder section 22. Further, the ladder section 22 supports three gantry-side converging electromagnets 13 which configure the gantry-side transport line 5B. The inlet-side support section 21 and the ladder section 22 are connected to the shaft holding section 23 having a cylindrical shape.

The shaft holding section 23 is a cylindrical site which holds a shaft portion 23a protruding along the central axis line CL. The central casing section 24 to which a front end of the ladder section 22 is connected is connected onto the shaft holding section 23.

The central casing section 24 is a casing-shaped frame site which supports the second gantry-side deflection electromagnet 14, the first scanning electromagnet 15, and the third gantry-side deflection electromagnet 16 which configure the gantry-side transport line 5B. The central casing section 24 is connected to the leading end casing section 25 in the extending direction of the central axis line CL.

The leading end casing section 25 is a casing-shaped frame site configured so as to surround the fourth gantry-side deflection electromagnet 18. The leading end casing section 25 is located in the vicinity of the outer periphery of the enclosure 2. The leading end casing section 25 supports the second scanning electromagnet 17 and the fourth gantry-side deflection electromagnet 18 which configure the gantry-side transport line 5B. A portion of the leading end casing section 25 goes around to the front side of the enclosure 2 and has a shaft portion 25a protruding along the central axis line CL.

The first bearing section 26 and the second bearing section 27 are fixed to the building 100 and support the gantry 6 so as to be able to oscillate around the central axis line CL. The first bearing section 26 and the second bearing section 27 are disposed before and after the enclosure 2 so as to sandwich the enclosure 2 therebetween.

The first bearing section 26 is provided between the inlet section P of the gantry-side transport line 5B and the enclosure 2 and located on the rear side of the enclosure 2. The first bearing section 26 is fixed to a wall portion 102 provided in the irradiation chamber A and rotatably supports the shaft portion 23a of the shaft holding section 23.

The second bearing section 27 is provided on the side opposite to the first bearing section 26 with respect to the enclosure 2 and located on the front side of the enclosure 2. The second bearing section 27 is fixed to a wall of the irradiation chamber A and rotatably supports the shaft portion 25a of the leading end casing section 25.

Further, the charged particle beam irradiation apparatus 1 is provided with a counterweight 30 for balancing the oscillation of the gantry 6. The counterweight 30 is disposed so as to be located on the side opposite to the central casing section 24 with respect to the central axis line CL. The counterweight 30 is connected to the gantry 6 through a counterweight connection section 31.

The counterweight connection section 31 is a site connecting the gantry 6 and the counterweight 30 and is provided between the inlet section P of the gantry-side transport line 5B and the enclosure 2. The counterweight connection section 31 is located on the rear side of the first bearing section 26.

The counterweight connection section 31 shares a portion of the cylindrical shaft holding section 23 configuring the gantry 6. The shapes or the weights of the counterweight 30 and the counterweight connection section 31 are appropriately selected according to a balance with the gantry 6.

According to the charged particle beam irradiation apparatus 1 related to this embodiment described above, since the first and second bearing sections 26 and 27 supporting the gantry 6 are provided at positions to sandwich the enclosure 2 therebetween, compared to the apparatus of the related art in which a bearing section is provided on only one side of the enclosure 2, it is possible to accurately retain the gantry 6 in the vicinity of the enclosure 2 and the irradiation section 3. As a result, since it is possible to suppress a deviation of the isocenter position of the irradiation section 3 due to a change in the angle of the gantry 6, it is possible to improve the isocenter accuracy of the apparatus. Further, since the enclosure 2 has the tubular side wall 2a extending along the central axis line CL and the opening portion 2c provided at a portion of the side wall 2a, a patient can enter the enclosure 2 from the side of the enclosure 2 rather than from a direction along the central axis line CL. That is, it is not necessary to provide a space for a patient to enter the enclosure 2 on the end portion side in the direction along the central axis line CL of the charged particle beam irradiation apparatus 1 in the irradiation chamber A. By installing the second bearing section 27 in the space which becomes omissible, it is possible to suppress an increase in the size of the irradiation chamber A in the direction along the central axis line CL and improve the isocenter accuracy of the apparatus.

In addition, according to the charged particle beam irradiation apparatus 1, in a case where the irradiation chamber A has a rectangular shape, if the gantry 6 is disposed in the irradiation chamber A such that the central axis line CL follows one diagonal line of the irradiation chamber A, since a patient can enter the enclosure 2 by using a space in a direction along the other diagonal line, an increase in the size of the irradiation chamber A can be further suppressed.

Further, according to the charged particle beam irradiation apparatus 1, since the counterweight connection section 31 is disposed at an area between the inlet section P of the gantry-side transport line 5B and the enclosure 2 where it is easy to secure a space in a design, it is also advantageous for a reduction in the size of the entire apparatus while balancing and stabilizing the oscillation of the gantry 6 around the central axis line CL.

The present invention is not limited to the embodiment described above. For example, a bearing section may be added to the rear of the first bearing section 26. Further, the shape or the configuration of the bearing section is not limited to that shown in the embodiment described above.

Further, the gantry 6 is not limited to a gantry which oscillates in the angular range shown in the embodiment described above, and an aspect in which the gantry 6 oscillates in another angular range is also acceptable and an aspect in which the gantry 6 rotates 360° is also acceptable. Further, the configuration of the gantry 6 or the transport line 5 is not limited to that shown in the embodiment described above.

The present invention can be used as a charged particle beam irradiation apparatus in which it is possible to improve isocenter accuracy.

It should be understood that the invention is not limited to the above-described embodiment, but may be modified into various forms on the basis of the spirit of the invention. Additionally, the modifications are included in the scope of the invention.

What is claimed is:

1. A charged particle beam irradiation apparatus comprising:
    an irradiation section configured to irradiate a body with a charged particle beam;
    a gantry in which the irradiation section is disposed and which can rotate or oscillate around a central axis line;
    an enclosure which has a tubular side wall extending along the central axis line, vertical walls provided at both ends in a direction along the central axis line of the side wall, and an opening portion provided at a portion of the side wall and in which an irradiated body is disposed inside thereof; and
    a gantry-side transport line that has an inlet section on which the charged particle beam emitted from an accelerator is incident and that is supported by the gantry and configured to transport the charged particle beam incident from the inlet section, to the irradiation section,
    wherein the gantry has
    a first bearing section which is provided between the inlet section of the gantry-side transport line and the enclosure and supports the gantry so as to be able to rotate or oscillate, and
    a second bearing section which is provided on a side opposite to the first bearing section with respect to the enclosure and supports the gantry so as to be able to rotate or oscillate.

2. The charged particle beam irradiation apparatus according to claim 1, wherein the gantry is disposed in a rectangular irradiation chamber such that the central axis line follows one diagonal line of the irradiation chamber.

3. The charged particle beam irradiation apparatus according to claim 1, further comprising:
    a counterweight configured to balance rotation or oscillation of the gantry; and
    a counterweight connection section which is disposed between the inlet section of the gantry-side transport line and the enclosure and connects the gantry and the counterweight.

* * * * *